United States Patent [19]

Sato et al.

[11] Patent Number: 5,311,292
[45] Date of Patent: May 10, 1994

[54] TRANSMISSIVITY MEASURING APPARATUS FOR A COLOR SEPARATION PRISM

[75] Inventors: Tatsumi Sato, Oyamazakicho; Osamu Ando, Kyoto, both of Japan

[73] Assignee: Shimadzu Corporation, Kyoto, Japan

[21] Appl. No.: 915,599

[22] Filed: Jul. 21, 1992

[30] Foreign Application Priority Data

Aug. 29, 1991 [JP] Japan .................. 3-212836

[51] Int. Cl.⁵ .................. G01N 21/25; G01J 3/46
[52] U.S. Cl. .................. 356/406; 356/425
[58] Field of Search .................. 356/402, 406, 425

[56] References Cited

U.S. PATENT DOCUMENTS

| 4,762,412 | 8/1988 | Ohkubo et al. | 356/319 |
| 5,106,190 | 4/1992 | Fukuma | 356/325 |
| 5,164,788 | 11/1992 | Yoshikawa | 356/346 |

Primary Examiner—Robert J. Warden
Assistant Examiner—Christopher Y. Kim
Attorney, Agent, or Firm—Oliff & Berridge

[57] ABSTRACT

An apparatus for measuring color transmissivities of a color separation prism P includes (where the color separation prism P receives a measurement light S on an incident path and emits three color lights Sr, Sg and Sb on three exit paths of different directions): a photomultiplier 21 and an integrating sphere I for measuring an intensity of light entering the integrating sphere I on an entrance path, where the entrance path is set detached from an extension of the incident path; a first movable mirror 9 located in one of four paths including an extension of the incident path and the three exit paths for reflecting the light on each path to the second movable mirror 10; and a second movable mirror 10 placed on the entrance path of the integrating sphere I (with the photomultiplier 21) and oriented in one of four directions for reflecting the light from the first movable mirror 9 to the integrating sphere I. Because the 100%-transmission light and the three color lights transmitted through the color separation prism P undergo the same optical history, absolute transmissivities of the color lights can be measured, and the two-beam method can be used since the integrating sphere I is fixed.

13 Claims, 4 Drawing Sheets

100%-TRANSMISSION COLOR TRANSMISSIVITY

GREEN

RED

BLUE

TRANSMISSIVITY MEASURING APPARATUS FOR A COLOR SEPARATION PRISM

The present invention relates to an apparatus for measuring color transmissivities of a color separation prism used in video cameras, projectors, color copying machines, etc.

BACKGROUND OF THE INVENTION

A color separation prism is constructed as shown in FIG. 3, in which an incident light S is separated into three primary color lights, i.e., green light Sg, red light Sr and blue light Sb, and the three primary color lights Sg, Sr and Sb are emitted from the color separation prism P in different directions. Since the color separating quality of a separation prism is substantial in the color reproducing quality of video cameras, etc, it is important to measure the exact color separating quality of a color separation prism. But no appropriate apparatus is yet commercially available for measuring the color separating quality and no standard measurement apparatus is established. So, manufacturers or researchers have made the measurement apparatus by themselves when necessary, which is a time consuming and troublesome work for manufacturers or researchers of video camera, etc.

A simple prior art method for measuring color transmissivities of a color separation prism is shown in FIG. 4. In this method, an integrating sphere I for integrating light before measuring the intensity of light by a photometer (not shown) is moved among three locations respectively on the paths of the three color light beams emitted from a color separation prism P. But this method requires careful and troublesome relocating operations of the integrating sphere I (with a photometer). When a two-beam method, in which a reference light beam is measured simultaneously with a measurement light beam transmitted through a sample, is used, the path of the reference light has to be moved according to the three locations of the integrating sphere I and the photometer. Thus the method of FIG. 4 is difficult to apply to the two-beam method.

Another prior art method for measuring color transmissivities of a color separation prism is shown in FIG. 5. In this method, six mirrors M1 through M6 are rectangularly arranged between a color separation prism P to be measured and an integration sphere I (with a photometer not shown). When the transmissivity for green light of the color separation prism P is measured, the two mirrors M1 and M2 on the central axis are removed and the green light separated by the color separation prism P and emitted straight therefrom enter the integrating sphere I without being reflected by any of the mirrors M1-M6. When red transmissivity is measured, the red light emitted down-leftward from the color separation prism P is reflected by the mirrors M3, M4 and M2 before entering the integrating sphere I. In case of blue transmissivity measurement, the blue light emitted upper-leftward from the color separation prism P is reflected by the mirrors M5, M6 and M2 before entering the integrating sphere I.

Since, in this method, the integrating sphere I is fixed, the two-beam method can be used unlike the method shown in FIG. 4. But the green light enters the integrating sphere I without being reflected by any mirror while the red light and the blue light enter the integrating sphere after being reflected by mirrors M2, M3, M4, M5 or M6. That is, the three primary color lights do not undergo the same optical history. Thus a 100%-transmission measurement has to be made for every color light, which is time-consuming. Another drawback of this method is that the exact absolute transmissivity can be measured only for the green light: only relative transmissivities as to the reflectivity of the mirror M1 can be measured for the red and blue lights and no exact absolute transmissivity can be obtained.

SUMMARY OF THE INVENTION

The present invention constructs a transmissivity measuring apparatus for a color separation prism that eliminates such troublesome operations and can measure exact transmissivities of the three primary colors.

According to the present invention, an apparatus for measuring color transmissivities of a color separation prism comprises (where the color separation prism receives a measurement light on an incident path, and emits three color lights on three exit paths of different directions):

photomeasurement means for measuring an intensity of light coming on an entrance path, where the entrance path is set detached from an extension of the incident path;

a first movable mirror located in one of four paths including the extension of the incident path and the three exit paths for reflecting the light on each path to the second movable mirror; and a second movable mirror placed on the entrance path of the photomeasurement means and oriented in one of four directions for reflecting the light from the first movable mirror to the photomeasurement means.

Since the photomeasurement means does not move in the above construction, the present invention can be favorably applied to the two-beam method. In this case, the transmissivity measurement apparatus according to the present invention comprises:

a light source for generating a reference light and a measurement light;

photomeasurement means for measuring an intensity of light entering the photomeasurement means on an entrance path, where the entrance path is set detached from an extension of the incident path;

a reference optical system for guiding the reference light to the photomeasurement means;

an incident optical system for leading the measurement light to the color separation prism on the incident path;

a first movable mirror located in one of four paths including the extension of the incident path and the three exit paths for reflecting the light on each path to the second movable mirror; and a second movable mirror placed on the entrance path of the photomeasurement means and oriented in one of four directions for reflecting the light from the first movable mirror to the photomeasurement means.

The present invention can be applied to an adapter for a two-beam type spectrophotometer, which enables a normal spectrophotometer to measure color transmissivities of a color separation prism by attaching the adapter. The application of the present invention to an adapter is described later.

DETAILED DESCRIPTION OF A PREFERRED EMBODIMENT

Figure 1:
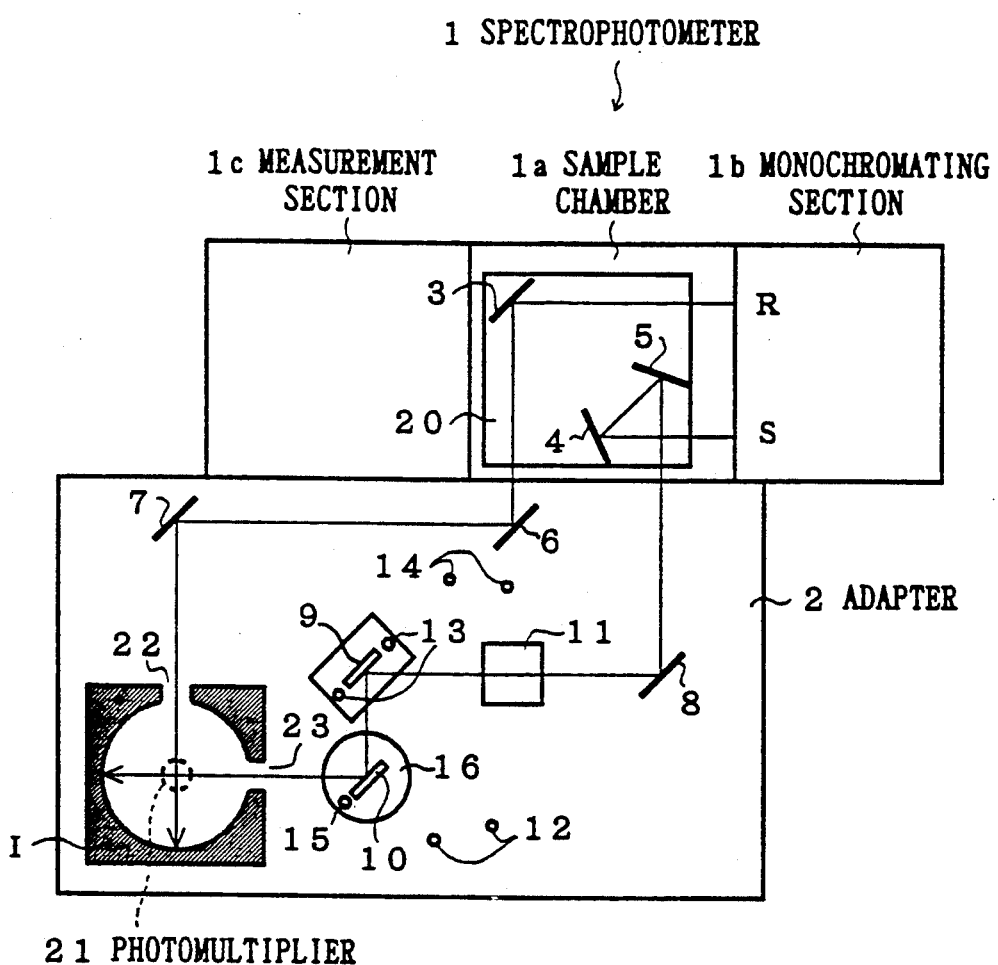
FIG. 1 is a plan view of an embodiment of the present invention.

An adapter for a spectrophotometer is described as an embodiment of the present invention. When color transmissivities of a color separation prism is measured, the adapter 2 is attached to a side end of a spectrophotometer 1 as shown in FIG. 1. The spectrophotometer includes: a sample chamber 1a in which a sample is normally placed; a monochromatic section 1b from which a scanning monochromated reference light beam R and a scanning monochromated sample light beam S are emitted; and a measurement section 1c in which the light from the sample in the sample chamber 1a is measured.

When the adapter 2 is attached to measure color transmissivities of a color separation prism, three mirrors 3, 4 and 5 are placed in the sample chamber 1a to extract the reference light beam R and the sample light beam S to the adapter 2. The three mirrors 3, 4 and 5 are fixed on a base 20 to form a unit, and the mirror unit is attached to the floor of the sample chamber 1a by an appropriate positioning pins (not shown), which facilitates the attachment of the adapter 2 to the spectrophotometer 1 and ensures the exact arrangement of their optical systems. The mirror unit is used not only for the color transmissivity measurement as described later, but it can also be used for other measurements utilizing the reference light beam R and the measurement light beam S outside of the sample chamber 1a of the spectrophotometer 1. Therefore the mirror unit is prepared as a general adapter of the spectrophotometer 1.

In the adapter 2, three fixed mirrors 6, 7 and 8, a sample base 11, two movable mirrors 9 and 10, an integrating sphere I and a photomultiplier 21 as the photomeasurement means are provided. The three fixed mirrors 6, 7 and 8, the sample base 11 and the integrating sphere I are fixed on a common base of the adapter 2, and the photomultiplier 21 is attached to a window at the top of the integrating sphere I. The first movable mirror 9 can be placed at one of three locations on the adapter base: first at the upper-left iocation of the sample base 11, second on the extension of the path from the fixed mirror 8 to the sample base 11, and third at the down-left location of the sample base 11. The first movable mirror 9 is fixed at each location by a pair of pins and corresponding holes 14, 13 and 12 formed on the adapter base. The second movable mirror 10 is rotatable about a vertical axis running through the center of the mirror 10, and the orientation of the mirror 10 can be fixed at three directions each corresponding to the three locations of the first movable mirror 9. The position of the second movable mirror 10 is fixed by a pin 15 penetrating through the base 16 of the second movable mirror 10 and corresponding holes (not shown) formed in the adapter base.

The reference light beam R extracted from the spectrophotometer 1 by the mirror 3 and introduced in the adapter 2 is reflected by the fixed mirrors 6 and 7 and enters the integrating sphere I from a side window 22. The measurement light beam S extracted from the spectrophotometer 1 by the mirrors 4 and 5 and introduced in the adapter 2 is reflected by the fixed mirror 8 and directed to the sample base 11. Here the optical axis of the measurement light beam S passing over the sample base 11 does not coincide with the path to any window of the integrating sphere I, whereby the measurement light beam S cannot enter the sphere I directly. In the case of FIG. 1 where a color separation prism P is not placed on the sample base 11, the measurement light beam S reflected by the mirror 8 is reflected twice by the movable mirrors 9 and 10, and enters the integrating sphere I from another side window 23. The configuration of FIG. 1 in which a color separation prism is absent is for measuring the intensity of the 100%-transmission light.

Figure 2A:
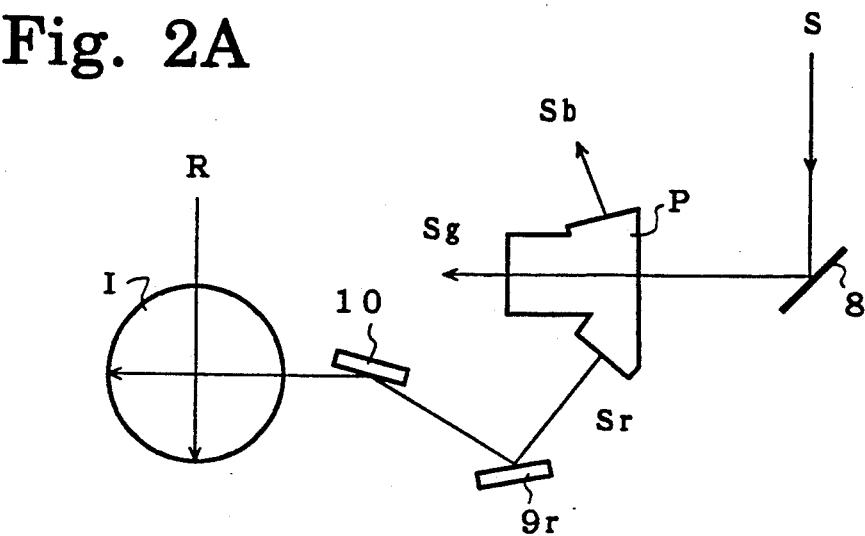
FIGS. 2A through 2C show plan views of the embodiment in measuring transmissivities of the three primary colors.
Figure 2B:
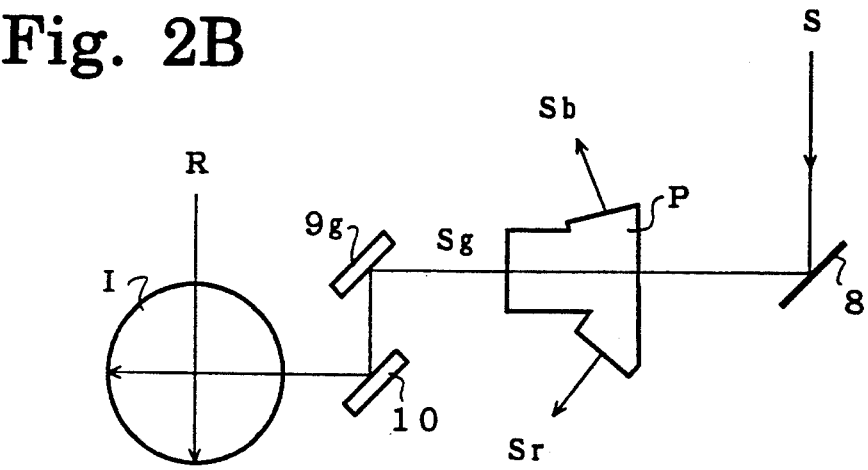
Figure 2C:
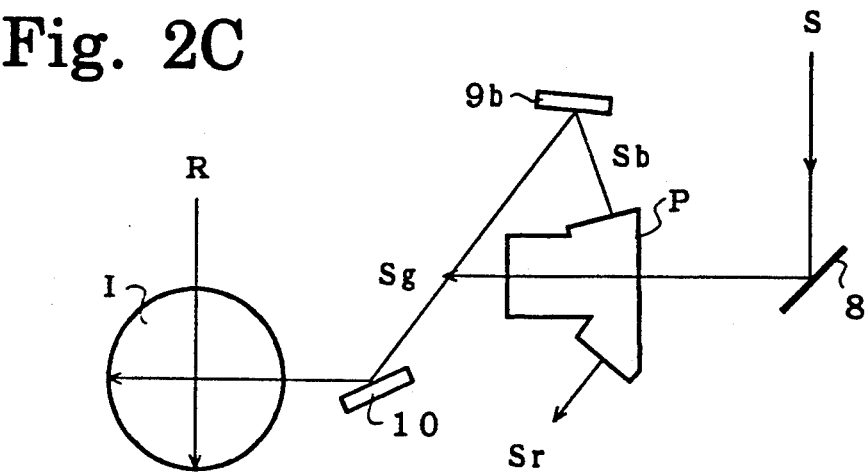
Figure 3:
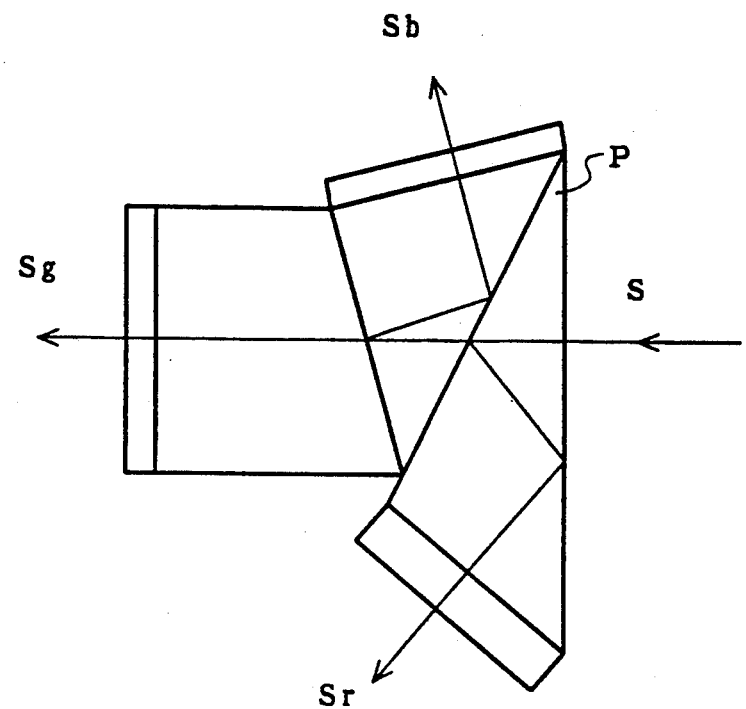
FIG. 3 is a cross-sectional view of a color separation prism.
Figure 4:
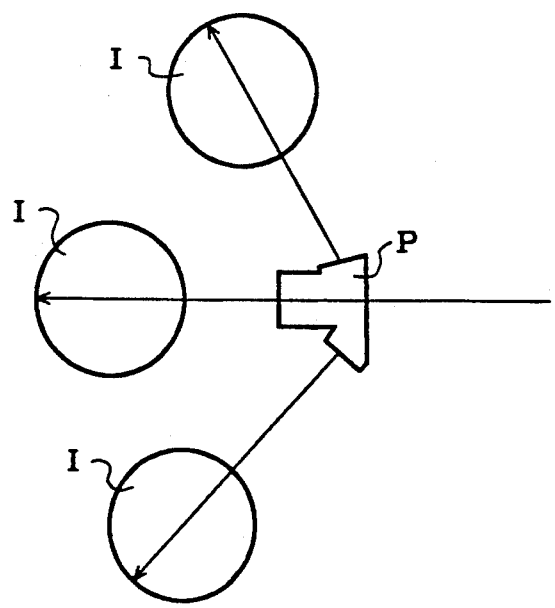
FIG. 4 shows a configuration of a color separation prism and an integrating sphere by a prior art method.
Figure 5:
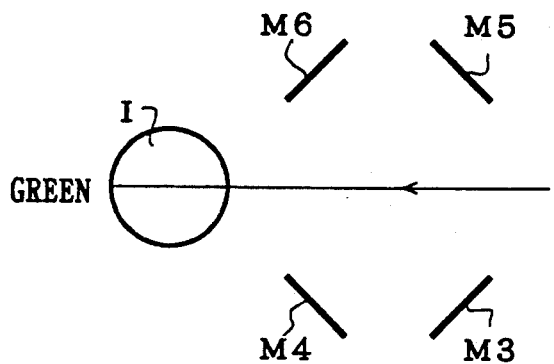
FIG. 5 shows configurations of a color separation prism, an integrating sphere and intervening mirrors by another prior art method.
Figure 5:
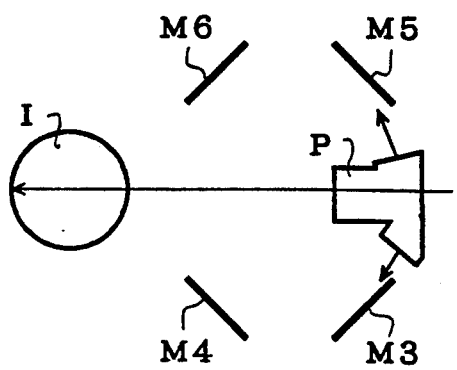
Figure 5:
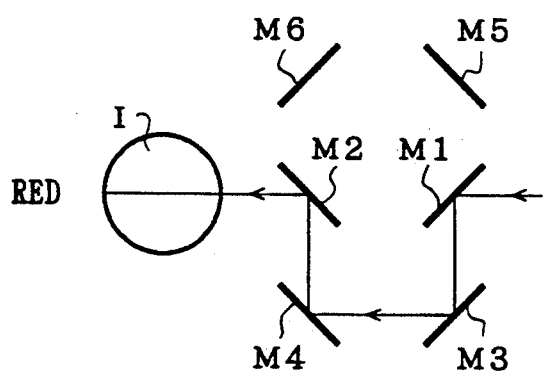
Figure 5:
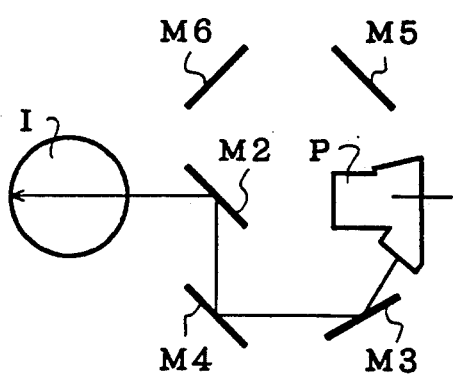
Figure 5:
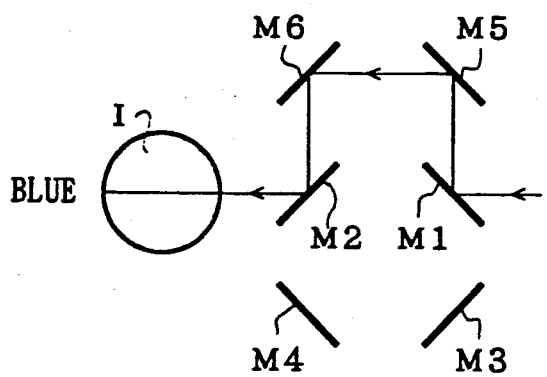
Figure 5:
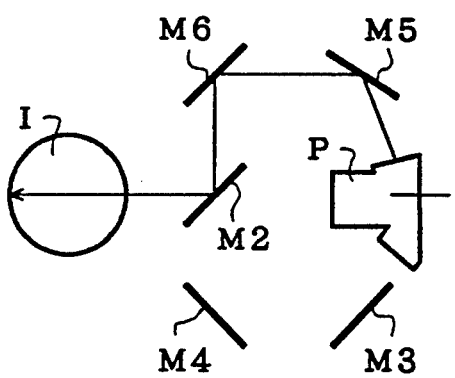

FIGS. 2A, 2B and 2C show the configurations for measuring the transmissivities of a color separation prism for the red, green and blue lights respectively. In these configurations, the movable mirror 9 changes its location, and the movable mirror 10 changes its orientation about a fixed axis. A sample color separation prism P is set on the sample base 11. In FIG. 2A, the first movable mirror 9 is placed at the location of the holes 12 (red position 9r). The red light beam Sr separated by the color separation prism P from the measurement light beam S and emitted down-leftward is reflected by the first movable mirror 9 in the red position 9r, and then reflected by the second movable mirror 10 which directs the red light beam Sr to the side window 23 of the integrating sphere I.

In the transmissivity measurement for the green light, the first movable mirror 9 is placed at the location of the holes 13 (green position 9g) as shown in FIG. 2B, and the second movable mirror 10 is oriented so that the green light Sg separated by the color separation prism P enters the integrating sphere I through the side window 23. In the present case where the color separation prism P emits the green light beam Sg straight with the incident measurement light beam S, the positions of the first and second movable mirrors 9 and 10 are the same as the case of the 100%-transmission measurement (FIG. 1).

In the transmissivity measurement for the blue light, the first movable mirror 9 is placed at the location of the holes 14 (blue position 9b) and the second movable mirror 10 is oriented as shown in FIG. 2C, whereby the blue light beam separated upper-leftward by the color separation prism P enters the integrating sphere I through the side window 23 via the movable mirrors 9 and 10.

In summary, the first and second movable mirrors 9 and 10 are placed and oriented in four positions, i.e., the 100%-transmission position (FIG. 1), the red position (FIG. 2A), the green position 9g (FIG. 2B which is the same as in FIG. 1 in this embodiment) and the blue position (FIG. 2C).

The integrating sphere I is used in the above embodiment because a stable measurement result can be obtained irrespective of change in thickness or of deviation of the path of the reference light beam R and the measurement light beam S. But it is of course possible to exploit the present invention without using the integrating sphere I.

Owing to the configuration of the present invention as shown in FIG. 1, the measurement light beam of the 100%-transmission measurement does not enter the integrating sphere I (or the photomultiplier 21) directly, but via two mirrors 9 and 10 as in the case of transmissivity measurements of the three color lights. Thus when the transmissivities are calculated by dividing the measured intensities of respective color lights by the intensity of the 100%-transmission light, the influence of the reflectivities of the mirrors are cancelled and exact absolute transmissivity values can be obtained. And since the integrating sphere I (and the photomultiplier 21) is fixed, the two-beam method can be applicable eliminating the influence of the change in the source light or in the photomeasurement circuit. The measuring operation is rather simple because the operator only needs to change the positions of the two mirrors 9 and 10. Since the number of mirrors is small and the photomultiplier 21 does not move, the adapter 2 can be small and low-cost. When the adapter 2 is not used, the spectrophotometer 1 is normally used.

What is claimed is:

1. An apparatus for measuring color transmissivities of a color separation prism which receives a measurement light on an incident path, the incident path defining an incident axis, the prism emitting one of three color lights on a corresponding one of three exit axes, each exit axis defining a line in a different direction, the apparatus comprising:
   photomeasuring means for measuring an intensity of light entering the photomeasuring means on an entrance path, the entrance path being displaced laterally from the incident axis;
   a first movable mirror movable to one of four first positions, each first position located along one of the incident axis and the three exit axes, the first movable mirror reflecting the light on the respective axis to a second movable mirror; and
   the second movable mirror placed on the entrance path of the photomeasuring means and movable to one of four second positions to reflect the light from the first movable mirror to the photomeasuring means.

2. The transmissivity measuring apparatus of claim 1, wherein one of the three exit axes lies along the incident axis.

3. The transmissivity measuring apparatus of claim 2, wherein the photomeasuring means includes an integrating sphere.

4. The transmissivity measuring apparatus of claim 3, further comprising a common base, and wherein
   the photomeasuring means and the integrating sphere are fixedly mounted to the common base;
   the first movable mirror is securable to the common base at each of the four first positions by a pair of pins and corresponding holes; and
   the second movable mirror is rotatable about a fixed axis and is securable to the common base at each second position by a pin and a corresponding hole.

5. An apparatus for measuring color transmissivities of a color separation prism which receives a measurement light on an incident path, the incident path defining an incident axis, the prism emitting one of three color lights on a corresponding one of three exit axes, each exit axis defining a line in a different direction, the apparatus comprising:
   a light source for generating a reference light and a measurement light;
   photomeasuring means for measuring an intensity of one of three color lights emitted by the prism entering the photomeasuring means on an entrance path, the entrance path displaced laterally from the incident axis;
   a reference optical system for guiding the reference light to the photomeasuring means;
   an incident optical system for guiding the measurement light to the color separation prism on the incident path;
   a first movable mirror movable to one of four first positions, each first position located along one of the incident axis and the three exit axes, the first movable mirror reflecting the light on the respective axis to a second movable mirror; and
   the second movable mirror placed on the entrance path of the photomeasuring means and movable to one of four second positions to reflect the light from the first movable mirror to the photomeasurement means.

6. The transmissivity measuring apparatus of claim 5, wherein one of the three exit axes lies along the incident axis.

7. The transmissivity measuring apparatus of claim 6, wherein the photomeasuring means includes an integrating sphere.

8. The transmissivity measuring apparatus of claim 7, further comprising a common base, and wherein
   the photomeasuring means and the integrating sphere are fixedly mounted to the common base;
   the first movable mirror is securable to the common base at one of the four first positions by a pair of pins and corresponding holes; and
   the second movable mirror is rotatable about a fixed axis and is securable to the common base at each second position by a pin and a corresponding hole.

9. An adapter attachable to a spectrophotometer for measuring color transmissivities of a color separation prism which receives a measurement light on an incident path, the incident path defining an incident axis, the prism emitting one of three color lights on a corresponding one of three exit axes, each exit axis defining a line in a different direction, the spectrophotometer having a light source for generating a reference light and the measurement light, the adapter comprising:
   extracting optical means located in the spectrophotometer for guiding reference light and measurement light from the spectrophotometer;
   photomeasuring means for measuring an intensity of light entering the photomeasuring means on an entrance path, the entrance path being displaced laterally from the incident axis;
   a reference optical system for guiding the reference light to the photomeasuring means;
   an incident optical system for guiding the measurement light to the color separation prism on the incident path;
   a first movable mirror movable to one of four first positions, each first position located along one of the incident axis and the three exit axes, the first movable mirror reflecting the light on the respective axis to a second movable mirror; and
   the second movable mirror placed on the entrance path of the photomeasuring means and movable to one of four second positions to reflect the light from the first movable mirror to the photomeasuring means.

10. The adapter of claim 9, wherein one of the three exit axes lies along the incident axis.

11. The adapter of claim 10, wherein the photomeasuring means includes an integrating sphere.

12. The adapter of claim 11, further comprising a common base, and wherein the photomeasuring means and the integrating sphere are fixedly mounted to the common base;

the first movable mirror is securable to the common base at one of the four first positions by a pair of pins and corresponding holes; and the second movable mirror is rotatable about a fixed axis and is securable to the common base at each second position by a pin and a corresponding hole.

13. The adapter of claim 12, where the extracting optical means includes a plurality of mirrors fixedly mounted on a base.

* * * * *

UNITED STATES PATENT AND TRADEMARK OFFICE
CERTIFICATE OF CORRECTION

PATENT NO. : 5,311,292
DATED : May 10, 1994
INVENTOR(S) : Tatsumi SATO and Osamu ANDO It is certified that error appears in the above-indentified patent and that said Letters Patent is hereby corrected as shown below:

Cover page, Item [30], change "August 29, 1991" to —July 29, 1991—.

Signed and Sealed this

Sixteenth Day of August, 1994

Attest:

BRUCE LEHMAN

Attesting Officer

Commissioner of Patents and Trademarks